United States Patent
Kim et al.

(10) Patent No.: US 10,627,416 B2
(45) Date of Patent: Apr. 21, 2020

(54) APTASENSOR FOR DETECTING FEMALE-SPECIFIC TRACE OF BLOOD AND DETECTION APPARATUS USING THE SAME

(71) Applicant: Republic of Korea(National Forensic Service Director Ministry of the Interior and Safety), Wonju-si, Gangwon-do (KR)

(72) Inventors: Joo Young Kim, Gwangju (KR); Pil Won Kang, Seoul (KR); Sang Ok Moon, Gimpo-si (KR); Man Il Kim, Gwangju (KR); Hye Hyeon Lee, Gyeongsan-si (KR); Hye Lim Kim, Gwangju (KR); Ki Won Park, Paju-si (KR); Yang Han Lee, Wonju-si (KR); Byung Won Chun, Wonju-si (KR)

(73) Assignee: REPUBLIC OF KOREA(NATIONAL FORENSIC SERVICE DIRECTOR MINISTRY OF THE INTERIOR AND SAFETY), Wonju-si, Gangwon-do (KR)

( * ) Notice: Subject to any disclaimer, the term of this patent is extended or adjusted under 35 U.S.C. 154(b) by 423 days.

(21) Appl. No.: 15/722,469

(22) Filed: Oct. 2, 2017

(65) Prior Publication Data
US 2018/0143209 A1    May 24, 2018

(30) Foreign Application Priority Data

Nov. 22, 2016  (KR) .................. 10-2016-0155389
Aug. 18, 2017  (KR) .................. 10-2017-0104805

(51) Int. Cl.
*G01N 33/74*  (2006.01)
*C12N 15/115* (2010.01)
(Continued)

(52) U.S. Cl.
CPC ......... *G01N 33/743* (2013.01); *C12N 15/115* (2013.01); *G01N 21/648* (2013.01);
(Continued)

(58) Field of Classification Search
CPC ............... G01N 33/743; G01N 33/542; G01N 33/5308; G01N 21/648; C12N 15/115; C12N 2310/16
See application file for complete search history.

(56) References Cited

FOREIGN PATENT DOCUMENTS

| KR | 10-2011-0075280 A | 7/2011 |
|---|---|---|
| KR | 10-2013-0044981 A | 5/2013 |

(Continued)

OTHER PUBLICATIONS

Doctor Korea, Forensics: Individual identification of blood markers, Forensics Story. Retrieved from www.doctorkorea.com on Dec. 9, 2017.

(Continued)

*Primary Examiner* — Sally A Merkling
(74) *Attorney, Agent, or Firm* — Novick, Kim & Lee, PLLC; Jae Youn Kim

(57) ABSTRACT

The present invention relates to an aptasensor for detecting a female-specific trace of blood including an aptamer which is used as a biosensor and emits light as the aptamer is bound to the female-specific trace of blood, and a detection apparatus using the same. The aptasensor for detecting a trace of blood to discriminate genders from the trace of blood at a crime scene has a configuration in which the aptasensor emits light as the aptasensor is binding to the female-specific trace of blood, so that genders of a suspect and a victim is distinguished from each other at the crime scene.

10 Claims, 8 Drawing Sheets
Specification includes a Sequence Listing.

(51) Int. Cl.
  *G01N 33/542* (2006.01)
  *G01N 21/64* (2006.01)
  *G01N 33/53* (2006.01)

(52) U.S. Cl.
  CPC ....... *G01N 33/5308* (2013.01); *G01N 33/542* (2013.01); *C12N 2310/16* (2013.01)

(56) References Cited

FOREIGN PATENT DOCUMENTS

| KR | 10-1459311 B1 | 11/2014 | | |
|---|---|---|---|---|
| KR | 10-2016-0086768 A | 7/2016 | | |
| KR | 1020160086768 | * | 7/2016 | ....... G01N 33/54326 |
| KR | 1020150136558 A | 1/2017 | | |

OTHER PUBLICATIONS

Nimet Yidirim et al., Aptamer-Based Optical Biosensor For Rapid and Sensitive Detection of 17 β-Estradiol In Water Samples, Environmental Science & Technology, Published on Jan. 31, 2012 , pp. 3288-3294, vol. 46.
Dr. Korea, Forensic Story _ Forensic Science: Individual Identification Blood Test, 2002.

\* cited by examiner

Aptamer-1 → Aptasensor-1

Aptamer-2 → Aptasensor-2

SEQUENCE LISTING

<160> NUMBER OF SEQ ID NOS: 4

<210> SEQ ID NO 1
<211> LENGTH: 66
<212> TYPE: DNA
<213> ORGANISM: Homo Sapiens

```
<220> FEATURE:
<223> OTHER INFORMATION: Aptamer 1

<400> SEQUENCE: 1
gcttcagctt attgaattac acgcagaggg tagcggctct gcgcattcaa ttgctgcgcg      60
ctgaag                                                                66

<210> SEQ ID NO 2
<211> LENGTH: 37
<212> TYPE: DNA
<213> ORGANISM: Homo Sapiens
<220> FEATURE:
<223> OTHER INFORMATION: Aptamer 2

<400> SEQUENCE: 2
aagggatgcc gtttgggccc aagttcggca tagtgtg                              37

<210> SEQ ID NO 3
<211> LENGTH: 101
<212> TYPE: DNA
<213> ORGANISM: Homo Sapiens
<220> FEATURE:
<223> OTHER INFORMATION: Aptasensor 1

<400> SEQUENCE: 3
cttccgcgtt ttttttttt tttttgctt cagcttattg aattacacgc agagggtagc       60
ggctctgcgc attcaattgc tgcgcgctga agcgcggaag c                        101

<210> SEQ ID NO 4
<211> LENGTH: 63
<212> TYPE: DNA
<213> ORGANISM: Homo Sapiens
<220> FEATURE:
<223> OTHER INFORMATION: Aptasensor 2

<400> SEQUENCE: 4
cacactatgt ttttttttt tttttaagg gatgccgttt gggcccaagt tcggcatagt       60
gtg                                                                   63
```

APTASENSOR FOR DETECTING FEMALE-SPECIFIC TRACE OF BLOOD AND DETECTION APPARATUS USING THE SAME

INCORPORATION OF SEQUENCE LISTING

This application contains a sequence listing submitted in Computer Readable Form (CRF). The CFR file containing the sequence listing is entitled "2-PK0051900-SeqListing", which was created and modified on Jan. 8, 2018, and is 1,369 bytes in size. The information in the sequence listing is incorporated herein by reference in its entirety.

BACKGROUND OF THE INVENTION

1. Field of the Invention

The present invention relates to an aptasensor for detecting a female-specific trace of blood, and more particularly, to an aptasensor for detecting a female-specific trace of blood including an aptamer which is used as a biosensor and emits light as the aptamer is bound to the female-specific trace of blood, and a detection apparatus using the same . . . .

2. Description of the Related Art

In general, evidences obtained from a crime scene take a great variety of forms. In the case of violent crimes such as robbery, rape and murder, the detection of traces of blood may provide a decisive clue to solve the case through serological analysis and gene identification, so that the detection of traces of blood can be an important clue at the crime scene.

In such detection of traces of blood, in case of most evidences of the crime scene, traces of blood of a suspect and a victim, who are involved in the case, are often mixed with each other or dispersed in various parts of the evidence. For this reason, when the gene identification is performed by collecting blood samples from the evidences of the crime scene, it is difficult to clearly determine the dispersion range of the mixed traces of blood and recognize individual traces of blood, so that a large quantity of samples is collected. Accordingly, very large analysis manpower and experimental expense are required.

Therefore, in the case that the genders of the suspect and victim are different from each other, since the most part of the required analysis manpower and experimental expense can be reduced if we develop a technique of distinguishing a specific trace of blood in the evidence of the crime scene, such a technique is necessary.

Meanwhile, a method of detecting a target substance by using antibodies has excellent sensitivity among various detection schemes used in the field of biosensors. Since the antibody is produced through an immune system of a living body, cell culture and an animal are required, and the purification process is performed to secure the antibody, a great deal of cost and time is required for the production. In addition, there are limited target substances that can be used as antigens as compared with an aptamer that has few constraints on target substances, so that it is difficult to produce antibodies against low molecular chemical substances such as toxic substances.

In general, since the antibody is a very large protein having a size of about 150K Da, there is a constraint on signal detection when the antibody is applied as an electrochemistry-based biosensor and the like, and chemical safety performance is significantly lower than DNAs or other chemical substances. In other words, the existing technique using the antibody to diagnose a biomarker in the blood is not cost and time efficient and has a range of application that is not broad, and there are constraints on applying the antibody as a biosensor.

A number of studies have been conducted for using an aptamer, which is a nucleic acid structure that exhibit specifically high affinity for various target substances, as a new sensing substance to improve these problems.

An aptamer is a single-stranded nucleic acid (DNA, RNA or modified nucleic acid) that has a stable tertiary structure all by itself, and has a feature of binding to a target molecule with high affinity and specificity. The term 'aptamer' originated from the Latin word 'aptus', which means 'fitting'. After an aptamer excavation technique called Systematic Evolution of Ligands by EXponential enrichment (SELEX) is firstly developed by the Larry Gold research team at the University of Colorado in 1990 (Ellington, A D and Szostak, J W. In vitro selection of RNA molecules that bind specific ligands, Nature 346:818-822 (1990)), a number of aptamers that can bind to various target molecules including low molecular organic matter, peptide, and even membrane protein have been developed. Aptamers are often compared to monoclonal antibodies due to their features of binding to a target molecule with high inherent affinity (usually in a pM level) and specificity. In addition, aptamers are especially called 'chemical antibody', which means that the possibility of using the aptamers as alternative antibodies is very high.

The application of the aptamer in the diagnosis and analysis is very natural because the aptamer has a target affinity comparable to that of antibodies, a size much smaller than that of antibodies, and an ability to bind to various target molecules with high binding force. After an aptasensor that optically detects 'human-neutrophill elastase' by using a fluorescent-labeled aptamer is firstly developed in 1997, an electrochemical sensor that responds by sensing the degree of electron transport appearing before and after the bonding of the aptamer to a target molecule, an optical sensor for fluorescence measurement of fluorescent substances and the like, and a mass spectrometric aptasensor for analyzing and measuring the mass difference that appears before and after the bonding of the aptamer to a target substance are mainly developed.

One example of the technology related to such an aptamer is disclosed in the following patent documents and the like.

For example, Patent document 1 discloses an aptamer, which is a nucleic acid structure that specifically binds to vaspin which is one of adipocyte-derived adipokines that can be used as a biomarker for type 2 diabetes, a method of preparing the aptamer, and a use of the aptamer.

In addition, Patent document 2 discloses a DNA aptamer specifically binding to glyphosate, which is one of the most widely-used agricultural pesticide because it is one of phospono amino acid-based non-selective herbicides having relatively low toxicity to mammals, a method of preparing the DNA aptamer, and a use of the DNA aptamer.

Further, Patent document 3 discloses a reagent kit for detecting a sex hormone, the reagent kit including: a first reagent including a sex hormone and a metal nanoprobe in which a Raman reporter is immobilized; and a second reagent including magnetic particles in which an antibody for detecting the sex hormone is immobilized, wherein the sex hormone is estrogen or testosterone.

DOCUMENT OF RELATED ART

Patent Document (Patent document 1) Korean Patent Registration No. 10-1200553 (registered on Nov. 6, 2012)
(Patent document 2) Korean Patent Registration No. 10-1338520 (registered on Dec. 2, 2013)
(Patent document 3) Korean Patent Application Publication No. 2016-0086768 (published on Jul. 20, 2016)

SUMMARY OF THE INVENTION

Although the development of aptamer in Korean is still in its early stage, researches for development and application of a new aptamer are actively conducted mainly in university research laboratories. However, most studies focus on the development of new pharmaceuticals as pharmaceutical preparations for treating cancer and immunological diseases, the development of in vitro diagnostic methods including a multiplex aptamer assay technique using a modified aptamer, the development of a molecular contrast material and the like. Since researches on the aptamer for the forensic field applicable to crime scenes are still lacking, it is necessary to conduct the aptamer researches for the forensic field.

To solve the problems described above, an object of the present invention is to provide an aptasensor for detecting a female-specific trace of blood and a detection apparatus using the same, which are capable of identifying the female-specific trace of blood by using an aptamer at a crime scene.

Another object of the present invention is to provide an aptasensor for detecting a female-specific trace of blood and a detection apparatus using the same, which are used for discriminating genders from a trace of blood at a crime scene to efficiently perform gene identification.

To achieve the objects described above, according to the present invention, there is provided an aptasensor for detecting a female-specific trace of blood to discriminate genders from a trace of blood at a crime scene, wherein the aptasensor emits light as the aptasensor is binding to the female-specific trace of blood.

In addition, according to the present invention, there is provided an aptasensor for detecting a female-specific trace of blood, wherein the binding may be implemented by 17β-estradiol.

In addition, according to the present invention, there is provided an aptasensor for detecting a female-specific trace of blood, wherein the aptasensor may include a base sequence of

```
5'-6FAM-CTTCCGCGTTTTTTTTTTTTTTTGCTTCAGCTTATTGA
ATTACACGCAGAGGGTAGCGGCTCTGCGCATTCAATTGCTGCGCGCTGA
AGCGCGGAAGC-BHQ1-3'
or
5'-6FAM-
CACACTATGTTTTTTTTTTTTTTTTAAGGGATGCCGTTTGGGCCCAAG
TTCGGCATAGTGTG-BHQ1-3'.
```

In addition, according to the present invention, there is provided an aptasensor for detecting a female-specific trace of blood, wherein the aptasensor may have a hairpin structure.

In addition, according to the present invention, there is provided an aptasensor for detecting a female-specific trace of blood, wherein the aptasensor may include a fluorescent label having an absorption wavelength of 495 nm and an emission wavelength of 517 nm.

In addition, to achieve the objects described above, there is provided an apparatus for detecting a female-specific trace of blood by using an aptasensor, the apparatus including: a body which is shielded from an outside and into which a blood sample is inputted; a detection device for adding a reagent of the aptasensor to the body and generating a signal in response to the female-specific trace of blood; and a control device for controlling the body and the detection device with a preset algorithm.

In addition, there is provided an apparatus for detecting a female-specific trace of blood, wherein the body may include: a station for supporting the sample such that a position of the sample is changeable; and a shielding device for opening and closing the station.

In addition, there is provided an apparatus for detecting a female-specific trace of blood, wherein the body may include: a processing liquid container for storing a pretreatment solution added to the sample; and a sprayer for spraying the pretreatment solution.

In addition, there is provided an apparatus for detecting a female-specific trace of blood, wherein a concentration of the reagent of the aptasensor may be maintained at 20 pmole/ul.

In addition, there is provided an apparatus for detecting a female-specific trace of blood, wherein the detection device may include: a variable light source for selectively irradiating the sample with lights having various wavelengths; and a photodetector for detecting fluorescence generated from the sample.

In addition, there is provided an apparatus for detecting a female-specific trace of blood, wherein the detection device may include an SPR detector for inducing surface plasmon resonance.

As described above, according to the aptasensor for detecting the female-specific trace of blood and the detection apparatus using the same of the present invention, an aptamer that emits light as the aptamer is bound to the female-specific trace of blood is provided, so that genders of a suspect and a victim can be distinguished from each other at a crime scene.

In addition, according to the aptasensor for detecting the female-specific trace of blood and the detection apparatus using the same of the present invention, the genders of the suspect and victim can be distinguished from each other at the crime scene by a portable variable light source, so that the analysis manpower and experimental expense can be reduced.

DETAILED DESCRIPTION OF THE INVENTION

The above objects, other objects and novel features of the present invention will become more apparent by the description of the present specification and the accompanying drawings.

The term "aptasensor" used in the present invention refers to an aptamer used as a biosensor.

First, the basic concept according to the present invention will be described.

According to the present invention, an aptasensor for detecting a female-specific trace of blood is used for developing an aptamer capable of responding to the female-specific trace of blood.

As a result of examining female-specific estrogen as a target among hormones contained in a trace of blood, 17β-estradiol is identified as estrogen that occupies the largest portion in normal serum of female, and approximately 50 to 400 pmoles of 17β-estradiol are present. Based on this result, a total of two papers related to an aptamer selectively binding to 17β-estradiol are found. The first one relates to an aptamer, which is studied by a group of Kim et al. in 2007 (Yeon Seok Kim, Ho Sup Jung, Toshihiko Matsuura, Hea Yeon Lee, Tomoji Kawai, Man Bock Gu. (2007), Electrochemical detection of 17β-estradiol using DNA aptamer immobilized gold electrode chip. Biosensors and Bioelectronics; 22:2525-2531.), in which an aptamer having an ability to detect 17β-estradiol up to KD (dissociation constant) 25 nM is produced. Next, an aptamer is studied by a group of Omar A. A. et al. in 2015 (Omar A. Alsager, Shalen Kumar, Bicheng Zhu, Jadranka Travas-Sejdic, Kenneth P. McNatty, and Justin M. Hodgkiss. (2015), Ultrasensitive Colorimetric Detction of 17β-estradiol: The Effect of Shortening DNA Aptamer Sequences. Analytical chemistry; 87:4201-4209.), in which an aptamer having an ability to detect 17β-estradiol up to KD (dissociation constant) 14 nM is produced and reported.

In the present invention, as shown in Table 1 as follows, two aptamers are selected based on the above-mentioned papers, in which an aptasensor-1 is designed by using an aptamer-1 (Kim et al., 2007) and an aptasensor-2 is designed by using an aptamer-2 (Omar A. A. et al., 2015). The detection of 17β-estradiol is examined by using the above aptasensors, and finally, a female-specific trace of blood is identified in several traces of blood at the crime scene.

TABLE 1

| Aptamer | Sequence | Remarks |
|---|---|---|
| 1 | 5'-GCTTCAGCTTATTGAATTACACGCAGAGGGTAGC GGCTCTGCGCATTCAATTGCTGCGCGCTGAAG-3' (SEQ ID NO.: 1) | Kim et al., 2007 |
| 2 | 5'-AAGGGATGCCGTTTGGGCCCAAGTTCGGCATAGT GTG-3' (SEQ ID NO.: 2) | Omar A.A. et al., 2015 |

Hereinafter, an aptasensor for detecting a female-specific trace of blood according to the present invention will be described with reference to the drawings.

Figure 1:
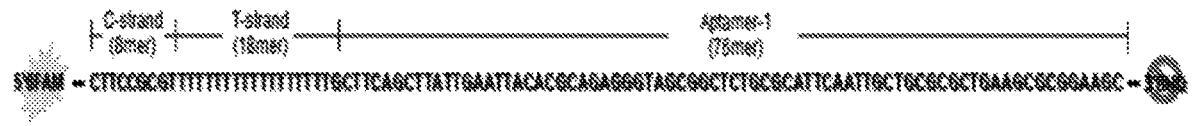
FIG. 1 is a schematic view showing an aptasensor-1 for detecting a female-specific trace of blood according to the present invention.
Figure 2:
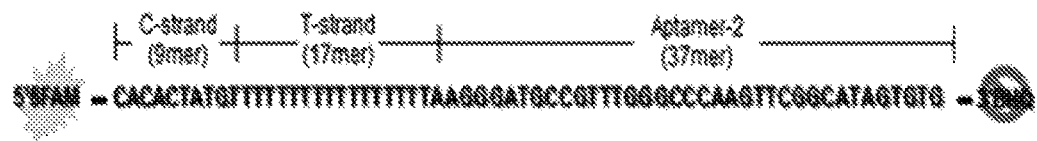
FIG. 2 is a schematic view showing an aptasensor-2 for detecting a female-specific trace of blood according to the present invention.

FIG. 1 is a schematic view showing an aptasensor-1 for detecting a female-specific trace of blood according to the present invention, and FIG. 2 is a schematic view showing an aptasensor-2 for detecting a female-specific trace of blood according to the present invention.

In relation to the aptasensor for detecting the trace of blood according to the present invention, a female-specific aptasensor is developed with reference to the above-described two papers. In addition, in order to develop an aptamer selectively binding to 17β-estradiol applied to the present invention, the selected aptamer is attached to gold nanoparticles (AuNPs) and the binding performance of the aptamer to 17β-estradiol is inspected. This method is difficult to be applied in the field of forensic science, which focuses on the crime scene, because the equipment capable of measuring a signal value over an electric electrode should be accompanied.

Therefore, in the present invention, in order to produce a female-specific aptasensor capable of performing the measurement more easily at the crime scene, an optical aptasensor having a fluorescent label selectively attached to two types of aptamers shown in Table 1 is designed. Such an optical aptasensor can be easily applied to the field-oriented forensic science field because 17β-estradiol can be easily detected using a portable variable light source.

The optical aptasensor applied in the present invention is firstly reported by a group of Hui et al. in 2011 (Hui Shi, Xiaoxiao He, Kemin Wang, Xu Wu, Xiaosheng Ye, Qiuping Guo, Weihong Tan, Zhihe Qing, Xiaohai Yang, and Bing Zhou. (2011), Activatable aptamer probe for contrast-enhanced in vivo cancer imaging based of cell membrane protein-triggered conformation alteration. PNAS; 108:3900-3905.), in which an optical aptasensor using an sgc8 aptamer that targets cell membrane protein tyrosine kinase-7 (PTK7) is produced, and the possibility of detecting PTK7 is inspected.

In the present invention, in order to produce the optical aptasensor as described above, a target molecule binding site of the aptasensor is replaced with a 17β-estradiol-specific aptamer, so that a total of two types of female-specific aptasensors are designed as shown in FIGS. 1 and 2.

In other words, as shown in FIGS. 1 and 2, the aptasensor-1 and the aptasensor-2 according to the present invention are provided with fluorescent labels on both ends of the aptasensors, so that the result can be easily obtained at the crime scene by an optical manner.

6-carboxyfluorescein (6-FAM), which is a fluorescent dye most commonly used as a forensic light source and has an absorption wavelength of 495 nm and an emission wavelength of 517 nm, is selected as the fluorescent label, and BHQ1, which is a fluorescent control product of Bioresearch Technology Corporation capable of inhibiting luminescence when the aptasensors are not bound to the target molecule, is attached to an end of 3' site.

Further, in order to produce the aptasensors in a hairpin structure to stabilize a structure according to the present invention, a C-strand base sequence, which is a mutual binding site, and a T-strand base sequence, which is a flexible site, are inserted, and an overall base sequence is shown in FIGS. 1 and 2, and Table 2 as follows.

Table 2 shows the base sequences of the aptasensor-1 and the aptasensor-2.

TABLE 2

| Aptasensor | Sequence |
|---|---|
| 1 | 5'-6FAM-CTTCCGCGTTTTTTTTTTTTTTTTGCTTCAGCTTATTGAATTACAC GCAGAGGGTAGCGGCTCTGCGCATTCAATTGCTGCGCGCTGAAGCGCGGAAGC (SEQ ID No.: 3)-BHQ1-3' |
| 2 | 5'-6FAM-CACACTATGTTTTTTTTTTTTTTTTAAGGGATGCCGTTTGGGCCCAA GTTCGGCATAGTGTG (SEQ ID No.: 4)-BHQ1-3' |

Hereinafter, the operation principle of the aptasensor-1 and the aptasensor-2 according to the present invention will be described with reference to FIG. 3.

Figure 3:
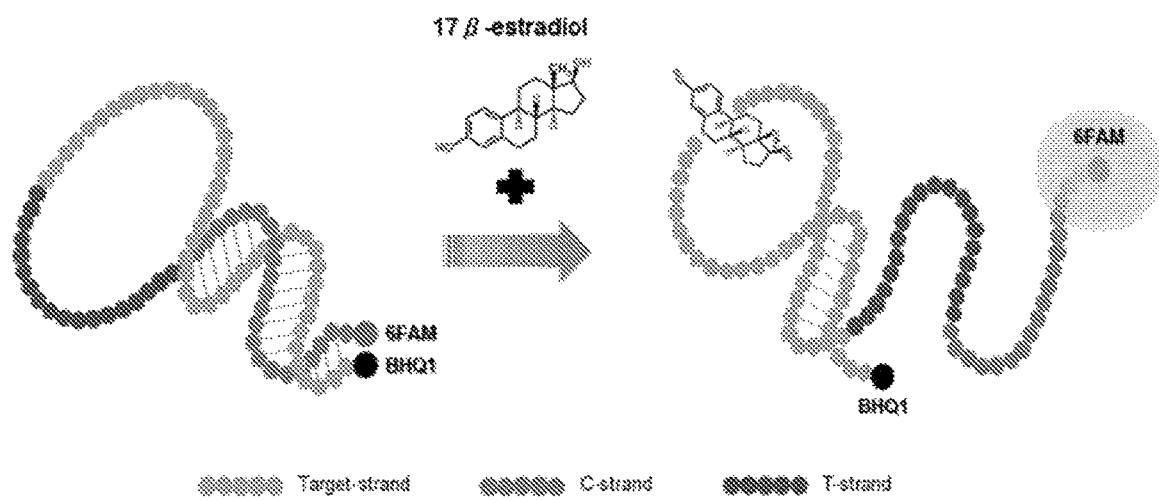
FIG. 3 is a view showing the operation principle of the aptasensor-1 and the aptasensor-2 according to the present invention.

FIG. 3 is a view showing the operation principle of the aptasensor-1 and the aptasensor-2 according to the present invention.

The optical 17β-estradiol-specific aptasensor developed in the present invention has the hairpin structure. Therefore, if the target substance (17β-estradiol) is not present, the fluorescent label 6FAM binds to the inhibitor BHQ1, so that light is not emitted even when a 495 nm light source irradiates the aptasensor. However, if 17β-estradiol is present, 17β-estradiol binds to the target site of the aptasensor, resulting in structural modification, so that the binding of the fluorescent label 6FAM and BHQ1 is separated. As a result, 6FAM emits light by the 495 nm light source.

Next, the structural stability prediction on the aptasensor-1 and the aptasensor-2 according to the present invention will be described with reference to FIG. 4.

Figure 4:
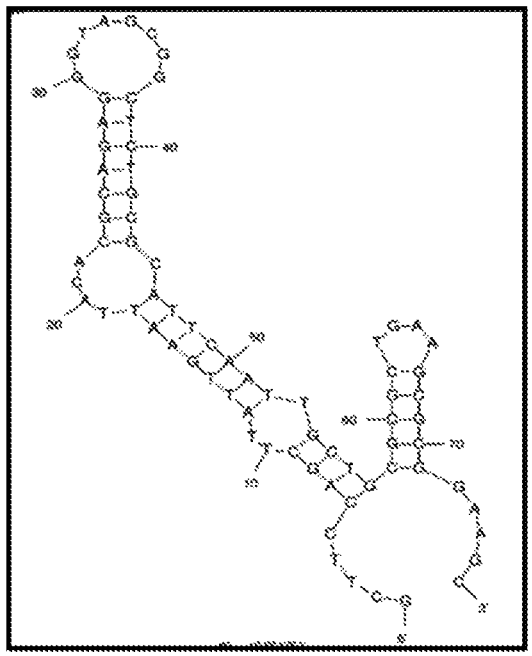
FIG. 4 is a view showing a structure of the aptasensor-1 and the aptasensor-2 according to the present invention.
Figure 4:
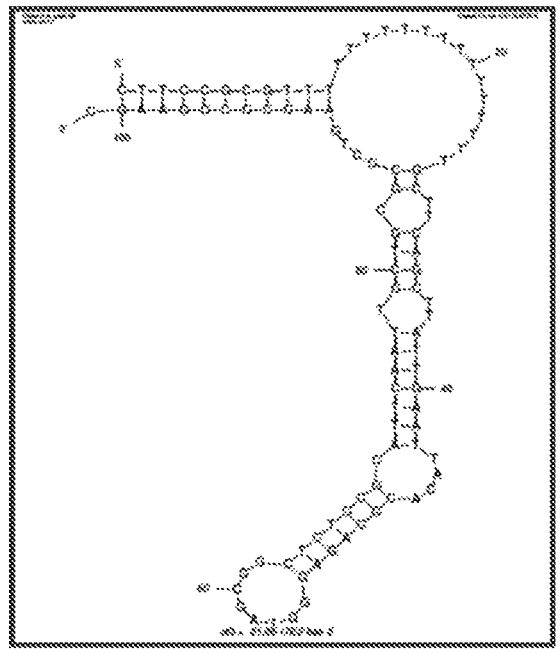
Figure 4:
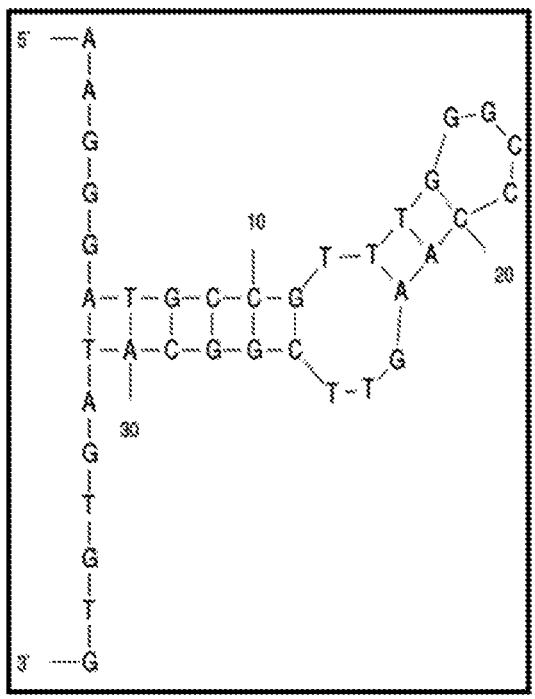
Figure 4:
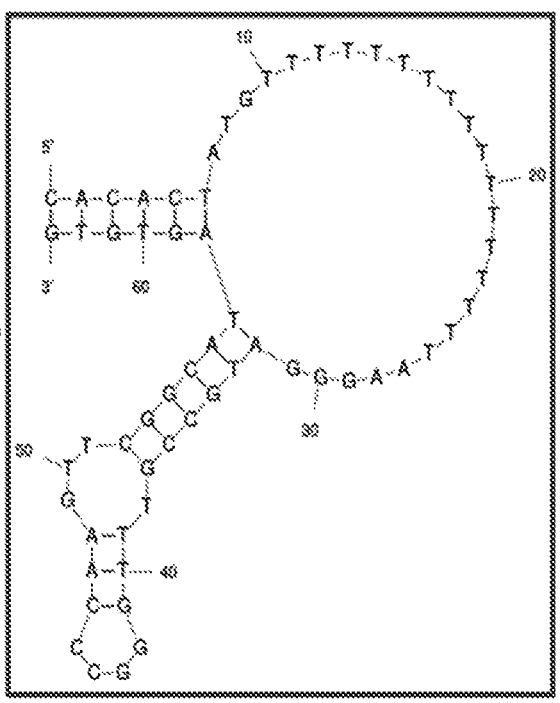

FIG. 4 is a view showing a structure of the aptasensor-1 and the aptasensor-2 according to the present invention.

The structural stability of the aptamer is particularly important in order to have high affinity and binding force with respect to target molecules. Further, in the present invention, since the optical aptasensor is firstly developed by additionally combining several base sequences to the previously-reported 17β-estradiol-specific aptamer, if the structure of a 17β-estradiol binding site of the aptasensor is changed due to the added base sequence, the optical aptasensor will not serve as an aptasensor.

To verify this, target-strand base sequence sites except for the C-strand and T-strand base sequence sites in the structure of the aptamer-1 and aptamer-2 of the previously-reported papers and the structure of the aptasensor-1 and aptasensor-2 developed in the present invention are compared with each other through an 'mfold' program which is a free-energy minimization algorithm. As a result, it is inspected that the structure is not changed as shown in FIG. 4.

According to another aspect of the present invention, an apparatus for detecting a female-specific trace of blood by using an aptasensor is proposed. About one drop of the trace of blood is sufficient as a sample of the trace of blood in both cases where the trace of blood is dried or not dried. The present invention is directed to, but not necessarily limited to, detect the female-specific trace of blood.

Figure 5:
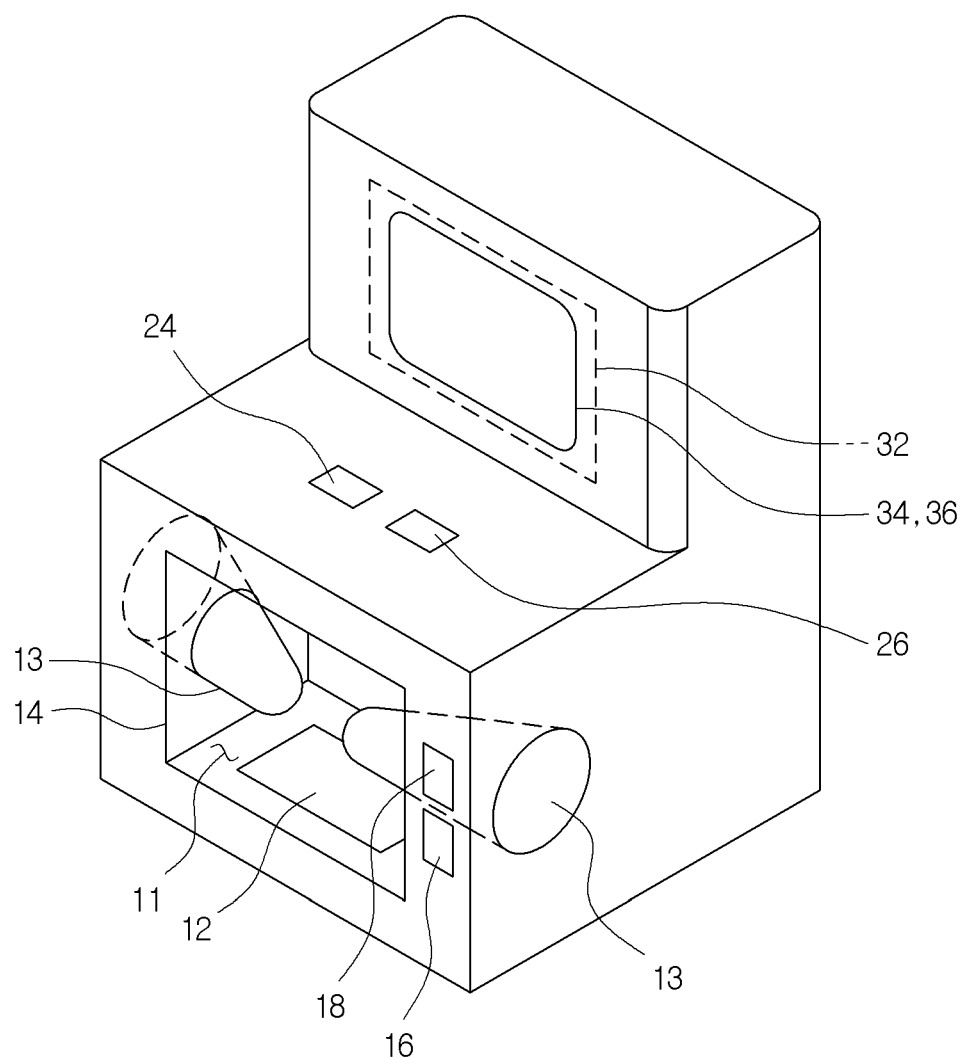
FIG. 5 is a schematic view schematically showing an apparatus according to the present invention.
Figure 6:
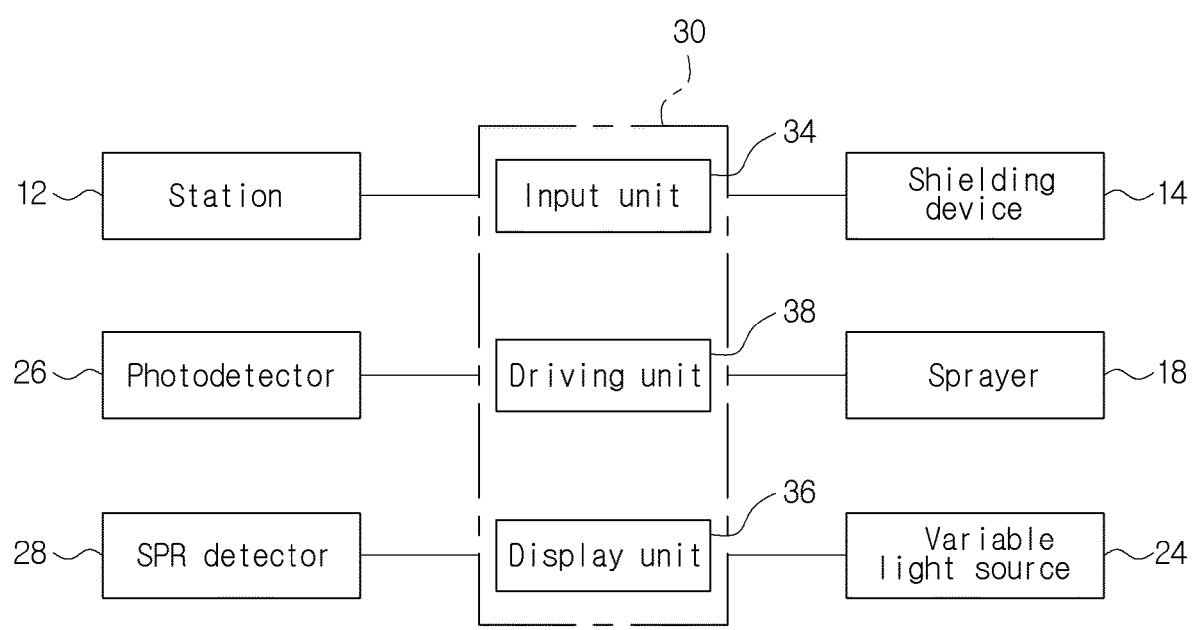
FIG. 6 is a block diagram showing a main circuit of the apparatus according to the present invention.

The main configuration of the present invention is shown in FIGS. 5 and 6.

According to the present invention, the body 10 has a structure in which a blood sample can be inputted and shielded from the outside. The body 10 has a structure that is easy to carry and maintains a stable posture. The body 10 has at least one input port 11 to input the sample. The shielding of the input port 11 is implemented such that it is useful to shield disturbance light or foreign substances.

The body 10 includes a station 12 for supporting the sample such that a position of the sample is changeable, and a shielding device 14 for opening and closing the station 12. The station 12 is installed to support the sample in a space adjacent to the input port 11. The station 12 may implement movement in at least one of an X axis, a Y axis, and a Z axis. The shielding device 14 includes a cover and a motor for opening and closing a space in which the station 12 is accommodated.

At this time, the aptasensor is stored in a processing liquid container 16 in the form of a reagent, and is sprayed to the sample by the sprayer 18. The sprayer 18 includes a pipe leading from the processing liquid container 16 to a spray nozzle, and a small pump for supplying the reagent.

Meanwhile, if the sample is a flexible object such as a cloth having the trace of blood, a separate sample table can be used to support the sample on the station 12. Reference numeral 13 that is not described denotes a gripping portion formed of a flexible material to manipulate the sample or reagent with a hand.

Figure 7A:
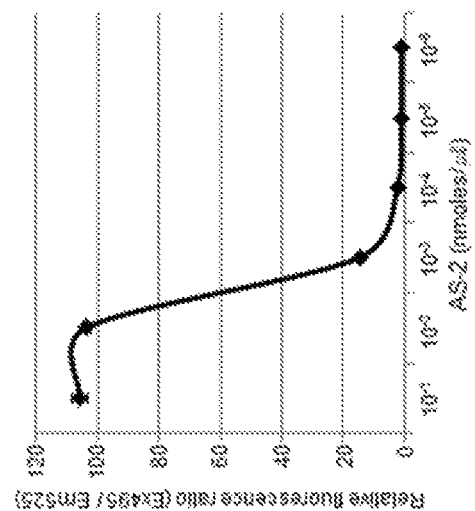
FIGS. 7A to 7C show result data of selecting a concentration of an aptasensor according to the present invention.
Figure 7B:
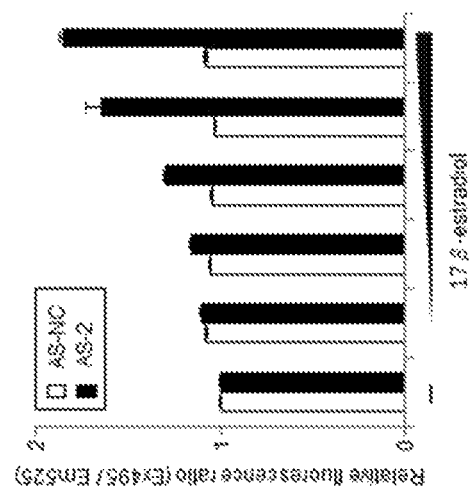
Figure 7C:
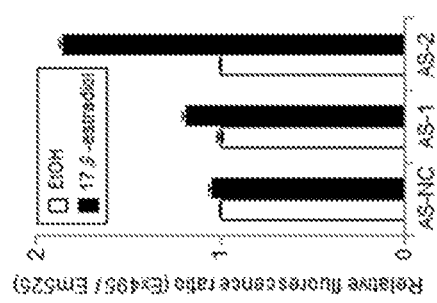

It is preferred that the concentration of the reagent of the aptasensor is maintained at 20 pmole/ul. In order to select a 17β-estradiol-specific aptasensor between the two types of aptasensors designed based on the information known in the art, examination is performed using 17β-estradiol and its solvent EtOH. As a result, it is inspected that the aptasensor-2 (hereinafter referred to as "AS-2") selectively reacts (see FIG. 7A). Moreover, it is inspected that the selective reaction is also increased as the concentration of 17β-estradiol increases (see FIG. 7B). Based on the above result, the concentration of AS-2 that is the most suitable for applying to the sample is found to be ideal at 20 pmole/ul (see FIG. 7C).

The body 10 may include: a processing liquid container 16 for storing a pretreatment solution added to the sample; and a sprayer 18 for spraying the pretreatment solution. The pretreatment solution may be a known substance for detecting the trace of blood, a known substance for enhancing the trace of blood and the like stored in the processing liquid container 16 separately from the aptasensor reagent for use. The sprayer 18 includes a separate pipe, and a small pump for supplying the pretreatment solution. Although omitted in the drawings, the body 10 may include a configuration for cleaning the station 12 and collecting the cleaning water.

Figure 8A:
FIGS. 8A to 8C show result data of inspecting applicability of the sensor according to the present invention.
Figure 8A:
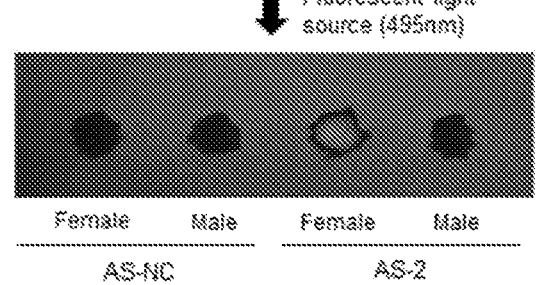
Figure 8B:
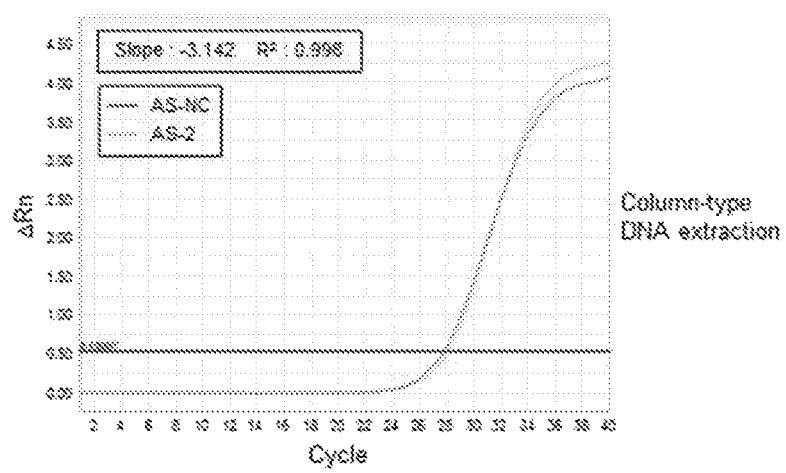
Figure 8C:
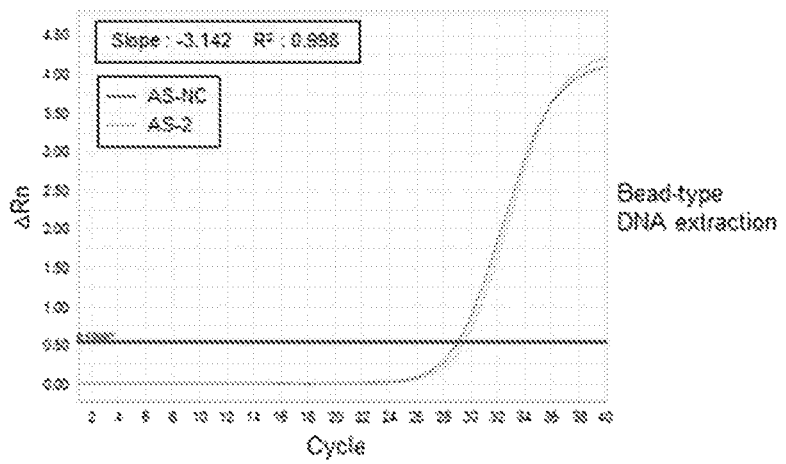

In addition, according to the present invention, a detection device 20 adds a reagent of the aptasensor to the body 10 and generates a signal in response to the female-specific trace of blood. In order to verify the applicability of the female-specific AS-2 in the trace of blood, the blood of female and male collected at the crime scene is left alone for one day at room temperature in the form of the trace of blood, AS-2 is processed, and the blood is examined by using a light source that emits light having a wavelength of 495 nm. As a result, the light emission is inspected only in the trace of blood of female (see FIG. 8A). In order to apply the female-specific AS-2, which has been inspected as described above, to the samples in the future, an area of the trace of blood that emits light is collected to perform the gene analysis thereon. To this end, DNA is extracted from the collected blood trace area by using two schemes. A first scheme is a DNA extraction scheme using a column (QIAamp Micro Kit, Qiagen), and a second scheme is a DNA extraction scheme using a bead (DNA IQ™ System, Promega). After performing the DNA extraction by applying both of the schemes, real-time PCR (Quantifiler Duo DNA Quantification Kit, Applied Biosystems) is performed. As a result, no interference due to fluorescence is observed in AS-2 compared with the control group (AS-NC) (see FIGS. 8B and 8C).

Figure 9A:
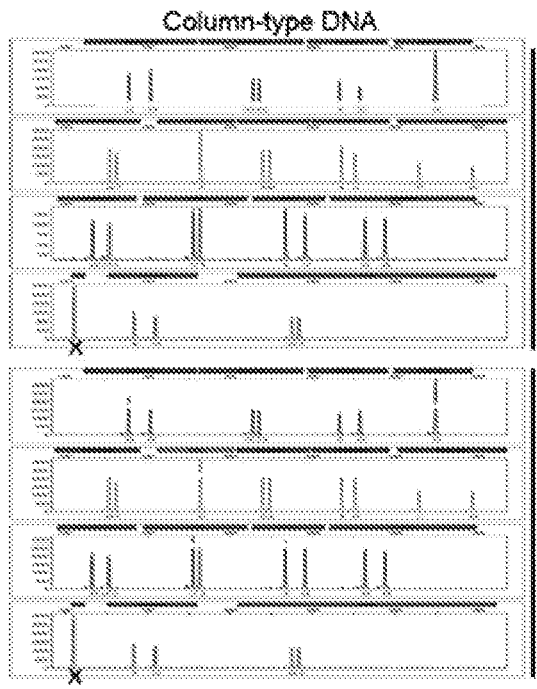
FIGS. 9A to 9D show result data of a gene analysis on a trace of blood performed by the sensor according to the present invention.
Figure 9B:
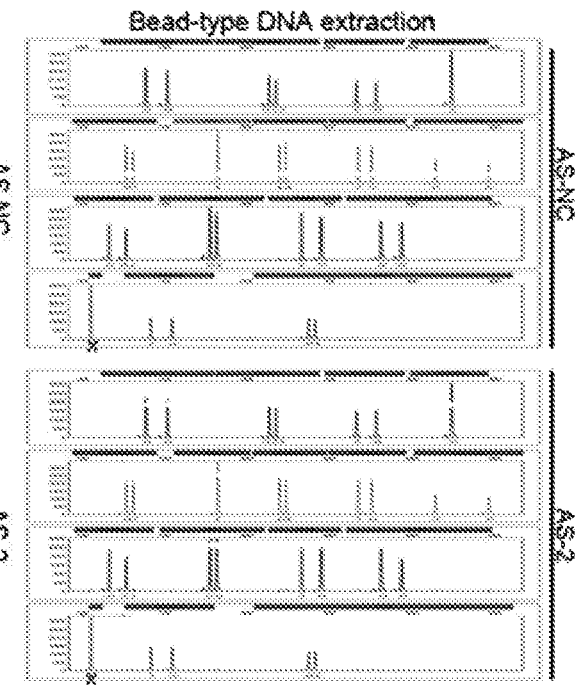
Figure 9C:
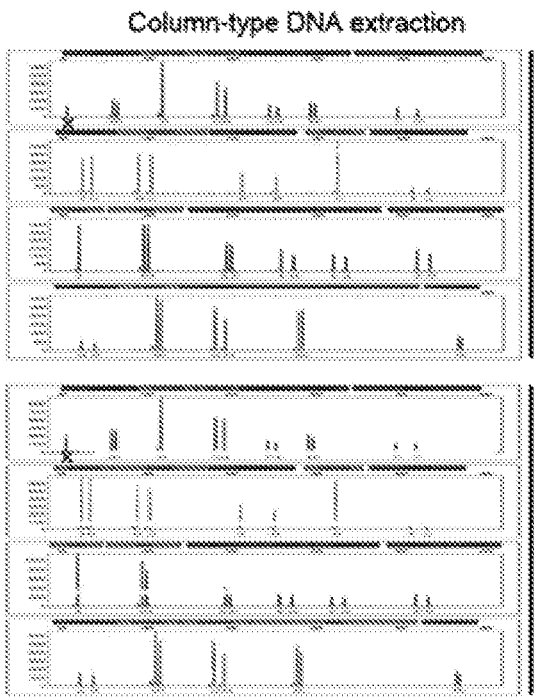
Figure 9D:
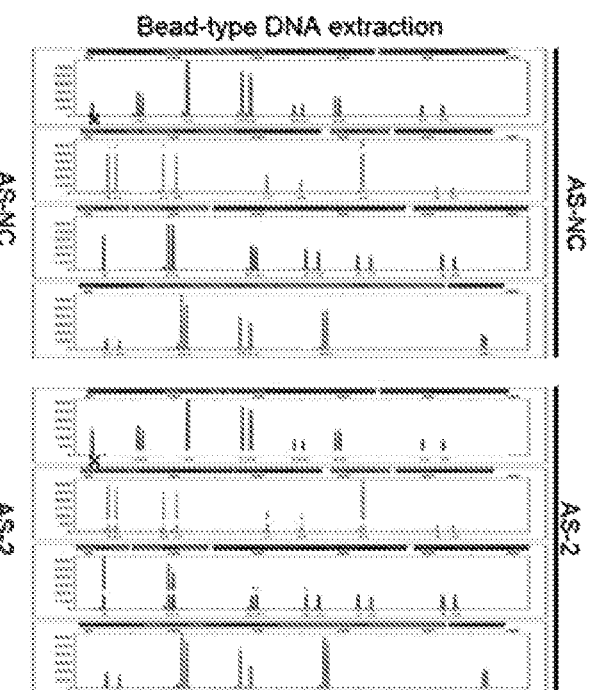

Two DNA extraction schemes are performed on the collected blood trace sites by using the female-specific AS-2, and the gene analysis is performed using an Identifiler Plus Kit (AmpFlSTR Identifiler Plus Kit, Applied Biosystems). As a result, the same tendency is observed in the control group (AS-NC) and the AS-2 treatment group, and especially in a green dye in which the fluorescence interference is predicted, so that it is observed that the AS-2 treatment has no influence on the gene analysis (see FIGS. 9A and 9B). In addition, a result obtained by using a PowerPlex Fusion Kit (PowerPlex Fusion System Kit, Promega) used for the cross experiment of the gene analysis shows that there is no influence similar to the above result (see FIGS. 9C and 9D).

The detection device 20 includes: a variable light source 24 for selectively irradiating the sample with lights having various wavelengths; and a photodetector 26 for detecting fluorescence generated from the sample. The variable light source 24 is configured such that an amplifier, a reflection filter, a mirror and the like are connected to a base laser diode (LD) having wide oscillation characteristics. An optical waveguide or optical fiber can be added to the variable light source 24 depending on the shape or standard of the body 10. The photodetector 26 is basically a CCD camera suitable for detecting fluorescence, and optionally includes a CMOS camera, a photomultiplier tube (PMT) and the like for additional functions.

According to a modification of the present invention, the detection device 20 may further include an SPR detector 28 for inducing surface plasmon resonance. In the case of applying the SPR detector 28, a laser light source device is installed in addition to the variable light source 24. Accordingly, the surface plasmon resonance (SPR) is induced in the sample so as to detect the specific reaction between molecules, the binding state, etc. The SPR detector 28 can be detachably attached to the body 10.

According to the present invention, a control device 30 controls the body 10 and the detection device 20 with a preset algorithm. The control device 30 is basically a controller 32 on which a microprocessor, a memory and an input/output interface is mounted. The detection device 20, the photodetector 26, the input unit 34, and the like are connected to the input interface. The input port 11, the shielding device 14, the sprayer 18, the variable light source 24, the display unit 36, and the like are connected to the output interface via a driving unit 38.

The control device 30 changes the wavelength of the variable light source 24, and processes a fluorescence signal. The controller 32 of the control device 30 adjusts the wavelength of the variable light source 24 to 495 nm by using an oscillation circuit of the driving unit 38, processes a signal generated by irradiating the sample with light through the photodetector 26, and displays the result in graphic and numerical data on the display unit 36 located at an upper portion of the body 10.

Figure 10A:
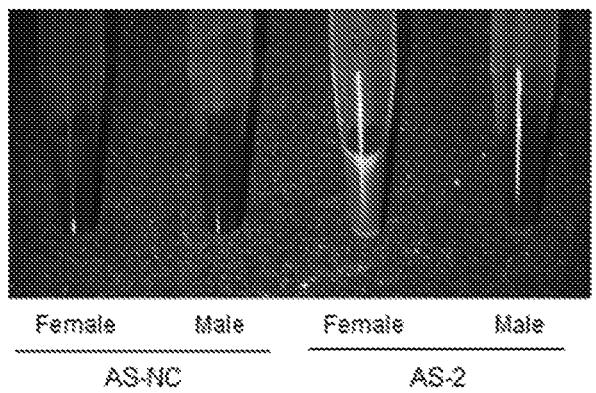
FIGS. 10A to 10D show result data of the operation performed by the apparatus according to the present invention.
Figure 10C:
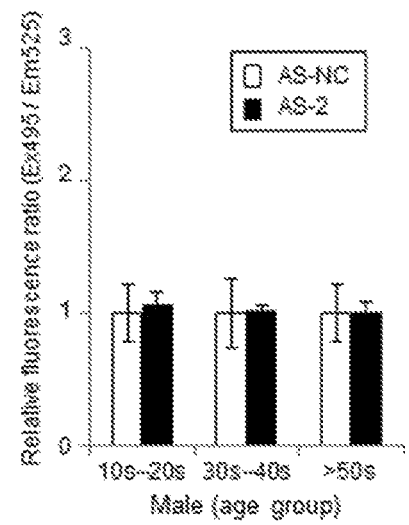
Figure 10B:
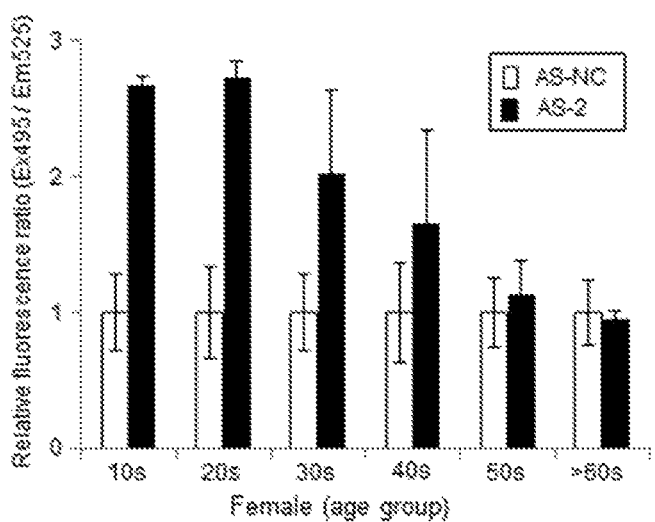
Figure 10D:
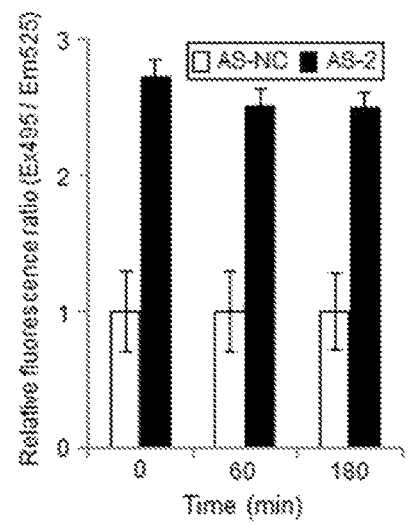

As an example of the operation, the female-specific detection probability of AS-2 is inspected using the blood of female and male collected at the crime scene by using the light having the wavelength of 495 nm provided by the variable light source 24. It is observed through the display unit 36 that the light emission specifically occurs in the trace of female blood treated with AS-2 (see FIG. 10A). In order to observe this in more detail, AS-2 is treated on female blood classified over age groups. As a result, in the blood of teenaged females to females in forties, it is detected 2-3 times more in the AS-2 treatment group than the control group (AS-NC). However, this phenomenon is remarkably decreased in the blood of females in fifties or more (see FIG. 10B), and the male blood did not show an increasing trend regardless of the age even though the AS-2 is treated, so that it is found that AS-2 acts female-specifically (see FIG. 10C). Furthermore, as the detection duration of AS-2 is inspected in the female blood, it is found that the detection limit is maintained for up to 3 hours, in which AS-2 stably acts without being decomposed in the blood (see FIG. 10D).

Although the present invention invented by the present inventor has been described in detail with reference to the embodiments, the present invention is not limited to the above embodiments, and various modifications are possible without departing from the scope and spirit of the present invention.

The present invention may be applied to distinguish genders of a suspect and a victim from each other at a crime scene by using the aptasensor for detecting the female-specific trace of blood and the detection apparatus using the same, which includes an aptamer that emits light as the aptamer is bound to the female-specific trace of blood.

What is claimed is:

1. An aptasensor for detecting a female-specific trace of blood to discriminate genders from a blood sample, wherein the aptasensor emits light as the aptasensor is binding to the female-specific trace of blood, and
wherein the aptasensor includes a base sequence of (SEQ ID NO.: 3)
5'-6FAM-CTTCCGCGTTTTTTTTTTTTTTTTTGCTTCAGCTTATTGA
ATTACACGCAGAGGGTAGCGGCTCTGCGCATTCAATTGCTGCGCGCTGA
AGCGCGGAAGC-BHQ1-3'
or (SEQ ID NO.: 4)
5'-6FAM-CACACTATGTTTTTTTTTTTTTTTTAAGGGATGCCGTTTG
GGCCCAAGTTCGGCATAGTGTG-BHQ1-3'.

2. The aptasensor of claim 1, wherein the binding is implemented by 17β-estradiol.

3. The aptasensor of claim 1, wherein the aptasensor has a hairpin structure.

4. The aptasensor of claim 1, wherein the aptasensor includes a fluorescent label having an absorption wavelength of 495 nm and an emission wavelength of 517 nm.

5. An apparatus for detecting a female-specific trace of blood by using an aptasensor, the apparatus comprising:

a body which is shielded from an outside and into which a blood sample is inputted;
a detection device for adding a reagent of the aptasensor to the body and generating a signal in response to the blood sample when the female-specific trace of blood is detected; and
a control device for controlling the body and the detection device with a preset algorithm,
wherein the aptasensor includes a base sequence of (SEQ ID NO.: 3)
5'-6FAM-CTTCCGCGTTTTTTTTTTTTTTTTTGCTTCAGCTTATTGAA

TTACACGCAGAGGGTAGCGGCTCTGCGCATTCAATTGCTGCGCGCTGAAG

CGCGGAAGC-BHQ1-3'
or (SEQ ID NO.: 4)
5'-6FAM-CACACTATGTTTTTTTTTTTTTTTTTAAGGGATGCCGTTTGG

GCCCAAGTTCGGCATAGTGTG-BHQ1-3'.

6. The apparatus of claim 5, wherein the body includes:
a station for supporting the blood sample such that a position of the blood sample is changeable; and
a shielding device for opening and closing the station.

7. The apparatus of claim 5, wherein the body includes: a processing liquid container for storing a pretreatment solution added to the blood sample; and a sprayer for spraying the pretreatment solution.

8. The apparatus of claim 5, wherein a concentration of the reagent of the aptasensor is maintained at 20 pmole/ul.

9. The apparatus of claim 5, wherein the detection device includes: a variable light source for selectively irradiating the blood sample with lights having various wavelengths; and a photodetector for detecting fluorescence generated from the blood sample.

10. The apparatus of claim 5, wherein the detection device includes an surface plasmon resonance (SPR) detector for inducing surface plasmon resonance.

\* \* \* \* \*